United States Patent [19]

Halpern et al.

[11] Patent Number: 4,722,867
[45] Date of Patent: * Feb. 2, 1988

[54] ALBUMIN-ENHANCED POLYSACCHARIDE SOLUTION

[76] Inventors: Gregory Halpern, Wilson Park Dr., Tarrytown, N.Y. 10591; Jack U. Gould, 500 E. 85th St., New York, N.Y. 10028

[*] Notice: The portion of the term of this patent subsequent to Apr. 14, 2004 has been disclaimed.

[21] Appl. No.: 4,406

[22] Filed: Jan. 20, 1987

Related U.S. Application Data

[63] Continuation-in-part of Ser. No. 852,602, Apr. 16, 1986, Pat. No. 4,657,820.

[51] Int. Cl.$^4$ .............................................. B32B 9/02
[52] U.S. Cl. ............................... 428/476.6; 428/515; 428/478.2
[58] Field of Search .................... 428/515, 478.2, 476.6

[56] References Cited

U.S. PATENT DOCUMENTS 4,411,832 10/1983 Cuatrecasas et al. ............... 260/121
4,448,718 5/1984 Yannas et al. ........................ 106/157
4,521,564 6/1985 Solomon et al. .................... 525/54.1
4,601,896 6/1986 Nugent .................................. 424/36
4,663,233 5/1987 Beavers ............................... 428/412

OTHER PUBLICATIONS

93:127469k An Interaction of Albumin with Hyaluronic Acid and Chondroitin Sulfate: A Study of Affinity Chromatography and Circular Dichroism., Gold, Edward W. (Coll. Med., Ohio State Univ., Columbus, Ohio 43210), Biopolymers 1980, 19(7), 1407-14 (Eng).

Primary Examiner—Theodore Morris
Attorney, Agent, or Firm—David H. Semmes; Warren E. Olsen

[57] ABSTRACT

Hydrophilic coating of plastics, particularly an enhanced aqueous solution of a polysaccharide which flows uniformly over the surface of an anchor film applied to the plastic. The aqueous solution of a polysaccharide from the group consisting of hyaluronic acid and its salts, chondroitin sulfate and agarose is enhanced by the addition of albumin to provide uniform wetting over the anchor film on the plastic.

5 Claims, No Drawings

ALBUMIN-ENHANCED POLYSACCHARIDE SOLUTION

CROSS-REFERENCES TO RELATED APPLICATIONS

A continuation-in-part of applicants' "ENHANCED POLYSACCHARIDE SOLUTION" (Ser. No. 852,602), filed Apr. 16, 1986, now U.S. Pat. No. 4,657,820.

The present application is directed to enhancing the aqueous solution of a polysaccharide, such as hyaluronic acid and its salts and chondroitin sulfate, by adding albumin in the range of 0.5% to 50% w/w on the polysaccharide. The enhanced solution provides uniform wetting over the surface of an anchor film applied to plastics.

BACKGROUND OF THE INVENTION (1) Field of the Invention

Hydrophilic coating of plastics, particularly a polysaccharide solution which is enhanced by adding albumin to provide improved wetting characteristics.

(2) Description of the Prior Art

Being submitted separately.

SUMMARY OF THE INVENTION

According to the present invention, aqueous solutions of polysaccharides from the group comprising hyaluronic acid and its salts, chondroitin sulfate, agarose and the like, are enhanced by adding albumin 0.5% to 50% on the polysaccharide to thoroughly wet the hydrophobic surface of a plastic, as well as the anchor film which may be applied to the plastic.

DESCRIPTION OF THE PREFERRED EMBODIMENTS

Polysaccharides such as hyaluronic acid and its salts confer a lubricious surface, when wet, to plastics, metals, and other hydrophobic materials. Thus, in the implantation of intraocular lenses, the surgeon will often ease the insertion of the harsh plastic lens by applying an aqueous solution of sodium hyaluronate to the wound. However, in such use, the polysaccharride is quickly washed away and the effect lost, and the need for a permanently effective lubricant has long been recognized.

As disclosed in a co-pending application entitled "LENS WITH HYDROPHILIC COATING", Ser. No. 791,021, lenses can be prepared with a permanently lubricious surface by applying a base coat with strong adhesion to the lens surface, followed by a top coat comprising a salt of a polysaccharide such as sodium hyaluronate, and grafting the two coats together by chemical reaction. For the lens application, the coating must have optical transparency and must transmit light without distortion of images. This can be achieved by proper combining of materials for the base coat and by insuring smooth conformation of the hydrophilic coating to the underlying surface; i.e., by good flow and leveling of the wet coating.

Experience has shown that the top coat, an aqueous solution of polysaccharide, will flow most uniformly and give most satisfactory optical quality if controlled amounts of albumin are added to the polysaccharide solution.

The mechanism by which this desirable result is achieved is not fully understood, but it is apparent that improved wetting of the first coat with improved continuity and uniformity of the second coat is the result. The albumin may cause reduction of the interfacial tension, or it may act as a cosolvent and cohesive agent for the polysaccharide. Whatever the mechanism, the combination is most efficacious in its practical value.

Applicants have determined that the minimum effective amount of albumin is characteristic of the grade of polysaccharide used, and in general is higher the purer the polysaccharide, as illustrated by the following examples. Even with quite crude grades of polysaccharide, a small amount of albumin such as 0.05% w/w is still desirable; with very pure grades, as much as 50% w/w on the polysaccharide may be efficacious.

EXAMPLE 1

On a clean, flat panel of polymethyl methacrylate was cast a 3-mil (wet) film of a solution coating comprising an acrylic polymer made from ethyl methacrylate, hydroxyethyl methacrylate, and methacrylic acid to which had been added a stoichiometric excess of a polyisocyanate. The panel was placed in a vacuum oven for 25 minutes at a temperature of 65° C. and pressure of 5 mm Hg, to remove most or all of the solvents present in the film. When removed from the oven and cooled to room temperature, the coating was clear, colorless and optically uniform.

EXAMPLE 2

To a panel prepared as in Example 1 was applied a 6-mil (wet) top-coat comprising a 1% aqueous solution of sodium hyaluronate (Sigma Chemical Company, Grade III). To a second panel prepared as in Example 1 was applied a 6-mil (wet) top-coat of the same composition except that 0.05% w/w on hyaluronate of human albumin (Sigma Chemical Company, crystallized, lyophilized, essentially globulin-free) was added. Both panels were placed in a vacuum oven at 65° C. and at atmospheric pressure for 20 minutes, after which the pressure was reduced to 5 mm Hg and held there for another 100 minutes. When removed and cooled to room temperature, the panels were compared by noting the wettability of the coatings with water. The first panel did not wet well along the edges of the coating, where the top-coat had crawled away from the acrylic coat, nor along several circular spots in the main expanse of the film. The second panel, to which albumin had been added, wetted uniformly over the entire area coated.

EXAMPLE 3

Panel A was prepared as in Example 1, and a top-coat was applied comprising a 0.1% aqueous solution of sodium hyaluronate supplied by the Medchem Company as an "Ultrapure" grade. Immediately after the casting knife and lifted from the panel, the aqueous coat crawled and gathered into strings and puddles of liquid, leaving large areas of the panel without a second coat. The heterogeneous panel resulting had very poor appearance and optical quality.

To more of the same aqueous solution was added 35% of albumin based on the weight of sodium hyaluronate present. This solution was applied to Panel B which had been prepared as in Example 1. The aqueous top-coat flowed smoothly and uniformly onto the base coat and after drying and curing gave a transparent panel with excellent optical quality and a high degree of lubricity when wet with water or synthetic tears.

EXAMPLE 4

A series of panels was prepared as in Example 1 and labled "A" through "F". A stock of aqueous solution was made up containing 0.1% of sodium hyaluronate offered by the Genzyme Company as a "Pharmaceutical" grade. To portions of this stock solution was added different amounts of albumin (as shown in Table 1), and top coats applied to Panels A through F, with the results given in Table I.

TABLE I

| Albumin Concentration | Quality of Top-Coat |
|---|---|
| 0% | Badly crawled |
| 0.5% | Badly crawled |
| 5% | Badly crawled |
| 10% | Crawling |
| 20% | Crawling |
| 30% | Slight Crawling |
| 50% | Excellent: no crawling |

EXAMPLE 5

To a panel prepared as in Example 1 was applied a top-coat consisting of a 13.5% solution of chondroitin sulfate in distilled water. The top-coat collected into droplets and puddles on the surface of the first coat. To another portion of the chondroitin sulfate solution was added 35% (on weight of the polysaccharide) of albumin. This latter solution produced a smooth, uniform film of excellent quality.

We claim:
1. A plastic object coated with:
   a. an acrylic polymer solution permitted to dry as an anchor coat, and
   b. an aqueous solution containing 0.1 to 13.5% of a polysaccharide from the group consisting of hyaluronic acid and chondroitin sulfate and 0.05 to 50% albumin w/w on said polysaccharide, applied as a top coat to said anchor coat.
2. A plastic object coated with:
   a. an acrylic polymer solution permitted to dry as an anchor coat, and
   b. an aqueous solution containing 0.1 to 1% sodium hyaluronate, and 0.5 to 50% albumin w/w on said hyaluronate, applied as a top-coat to said anchor coat.
3. A plastic object coated as in claim 2, wherein the acrylic polymer solution is 7.5 mole-percent hydroxyethyl methacrylate applied as a wet thickness of approximately 3 mils.
4. A plastic object coated as in claim 3, wherein said aqueous solution is applied as a top-coat as a wet thickness of at least 3 mils.
5. A plastic object coated with:
   a. an acrylic polymer solution permitted to dry as an anchor coat, and
   b. an aqueous solution containing approximately 13.5% of chondroitin sulfate, and approximately 35% of albumin on said chondroitin sulfate, applied as a top-coat to said anchor coat.

* * * * *